United States Patent [19]

Sauter et al.

[11] Patent Number: 5,334,607
[45] Date of Patent: Aug. 2, 1994

[54] METHODS FOR TREATING MYCOSES

[75] Inventors: Hubert Sauter, Mannheim; Gisela Lorenz, Neustadt; Gerd Steiner, Kirchheim; Bernd Janssen, Ludwigshafen; Timm Anke, Kaiserslautern; Wolfgang Steglich, Munich, all of Fed. Rep. of Germany

[73] Assignee: BASF Aktiengesellschaft, Ludwigshafen, Fed. Rep. of Germany

[21] Appl. No.: 889,418

[22] Filed: May 28, 1992

[30] Foreign Application Priority Data

May 28, 1991 [DE] Fed. Rep. of Germany ....... 4117371

[51] Int. Cl.$^5$ ..................... A01N 37/10; A01N 37/50; A01N 43/40; A01N 43/54; A01N 43/56
[52] U.S. Cl. ..................... 514/378; 514/267; 514/348; 514/403; 514/406; 514/522; 514/531; 514/532; 514/538; 514/617; 514/619; 514/626; 548/247; 560/35; 560/52; 560/55; 560/60
[58] Field of Search ........................... 560/35; 548/247; 514/378, 522, 538, , 531, 532, 348, 619, 403, 406, 267, 617, 626

[56] References Cited

U.S. PATENT DOCUMENTS

| | | | |
|---|---|---|---|
| 3,826,836 | 7/1974 | Buchel et al. | 424/273 |
| 4,937,372 | 6/1990 | Wenderoth et al. | 560/55 |
| 4,999,042 | 3/1991 | Anthony et al. | 560/35 X |
| 5,003,101 | 3/1991 | Brand et al. | 560/55 X |
| 5,021,581 | 6/1991 | Clough et al. | 546/309 |
| 5,041,618 | 8/1991 | Brand et al. | 560/104 |
| 5,051,447 | 9/1991 | Wenderoth et al. | 514/534 |
| 5,112,862 | 5/1991 | Wenderoth et al. | 514/522 |

FOREIGN PATENT DOCUMENTS

| | | | |
|---|---|---|---|
| 0253213 | 1/1988 | European Pat. Off. | 560/35 |
| 2172595 | 9/1986 | United Kingdom | 560/60 |
| 2192883 | 1/1988 | United Kingdom | 560/35 |

OTHER PUBLICATIONS

Godfrey et al., Chemical Abstracts, vol. 109, No. 110417t (1988).

Primary Examiner—Floyd D. Higel
Attorney, Agent, or Firm—Oblon, Spivak, McClelland, Maier & Neustadt

[57] ABSTRACT

Antimycotics containing a compound of the formula

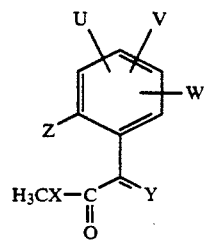

where
=Y is =CH—OCH$_3$, =CH—CH$_3$, =CH—CH$_2$—CH$_3$, =CH—SCH$_3$ or =N—OCH$_3$, and X is oxygen, or X may also be NH if Y is =N—OCH$_3$,
Z is halogen, nitro, cyano, unsubstituted or substituted organic radicals, OR$^{12}$, SR$^{13}$, SOR$^{14}$, SO$_2$R$^{15}$, —COOR$^{16}$, —CONR$^{17}$R$^{18}$, —COR$^{19}$, —CR$^{20}$=NR$^{21}$, —N=CR$^{22}$R$^{23}$, —CR$^{24}$=N—OR$^{25}$, —CR$^{25}$R$^{26}$—O—N=CR$^{27}$R$^{28}$ and
U, V, W can be hydrogen or one of the meanings given for Z, or where two of Z, U, V and W in adjacent positions on the phenyl ring can form an unsubstituted or substituted five- or six-membered, aromatic or aliphatic ring which may contain one to three hetero atoms (N, S, O), and R$^{12}$ to R$^{26}$ are identical or different and are hydrogen, unsubstituted or substituted organic radicals, are used for controlling mycoses.

6 Claims, No Drawings

METHODS FOR TREATING MYCOSES

The present invention relates to antimycotics which contain phenylacetic acid derivatives and to the use of these derivatives as antimycotics.

The use of phenylacetic acid derivatives as fungicides in crop protection has been disclosed (EP 178 826, 203 606, 203 608, 226 917, 229 974, 242 070, 242 081, 244 077, 251 082, 253 213, 254 426, 256 667, 260 794, 267 734, 270 252, 278 595, 280 185, 291 196, 299 694, 307 103, 310 954, 336 211, 337 211, 341 845, 342 459, 350 691, 354 571, 363 818, 370 629, 374 811, 378 308, 378 755, 379 098, 382 375, 385 224, 385 357, 386 561, 393 428, 393 861, 398 692, 400 417, 405 782, 422 597, 426 460, 459 285, 460 575, 463 488, 468 684, 468 695 and 468 775). There is no indication of an antimycotic action therein.

We have now found that compounds of the formula

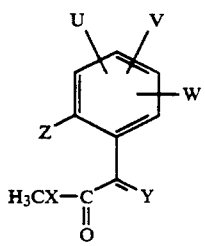

where
=Y is =CH—OCH$_3$, =CH—CH$_3$, =CH—CH$_2$—CH$_3$, =CH—SCH$_3$ or =N—OCH$_3$, X is oxygen or, if Y is =N—OCH$_3$, also NH, Z is halogen (F, Cl, Br, I), nitro, cyano, unsubstituted or substituted alkyl, unsubstituted or substituted cycloalkyl, unsubstituted or substituted aralkyl, unsubstituted or substituted aryloxyalkyl, unsubstituted or substituted arylthioalkyl, unsubstituted or substituted hetarylalkyl, unsubstituted or substituted hetaryloxyalkyl, unsubstituted or substituted hetarylthioalkyl, unsubstituted or substituted alkenyl, unsubstituted or substituted aralkenyl, unsubstituted or substituted aryloxyalkenyl, unsubstituted or substituted arylthioalkenyl, unsubstituted or substituted hetarylalkenyl, unsubstituted or substituted hetaryloxyalkenyl, unsubstituted or substituted hetarylthioalkenyl, unsubstituted or substituted alkynyl, unsubstituted or substituted aryl, unsubstituted or substituted hetaryl, unsubstituted or substituted amino, unsubstituted or substituted arylazo, unsubstituted or substituted acylamino, OR$^{12}$, SR$^{13}$, SOR$^{14}$, SO$_2$R$^{15}$, —COOR$^{16}$, —CONR$^{17}$R$^{18}$, —COR$^{19}$, —CR$^{20}$=NR$^{21}$, —N=CR$^{22}$R$^{23}$, —CR$^{24}$=N—OR$^{25}$, —CR$^{25}$R$^{26}$—O—N=CR$^{27}$R$^{28}$ and U, V, W are identical or different and can be hydrogen or one of the meanings given for Z, or where two of Z, U, V and W in adjacent positions on the phenyl ring can form an unsubstituted or substituted five- or six-membered, aromatic or aliphatic ring which may contain one to three hetero atoms (N, S, O), and R$^{12}$ to R$^{28}$ are identical or different and are hydrogen, unsubstituted or substituted C$_1$-C$_8$-alkyl, unsubstituted or substituted C$_2$-C$_8$-alkenyl, unsubstituted or substituted C$_2$-C$_8$-alkynyl, unsubstituted or substituted cycloalkyl, unsubstituted or substituted cycloalkylalkyl, unsubstituted or substituted aryl, unsubstituted or substituted hetaryl, unsubstituted or substituted aralkyl, unsubstituted or substituted hetarylalkyl, unsubstituted or substituted aryloxyalkyl, unsubstituted or substituted arylthioalkyl, unsubstituted or substituted hetaryloxyalkyl or unsubstituted or substituted hetarylthioalkyl, have a good antimycotic action. The compounds and the preparation thereof have been disclosed (see the European Laid-Open Applications mentioned at the outset).

One aspect of the invention relates to antimycotics which contain compounds of the formula 1 where U, V and W are identical or different and are hydrogen, fluorine, chlorine, bromine, iodine, cyano, nitro, trifluoromethyl, methyl or methoxy.

Another aspect of the invention relates to antimycotics which contain compounds of the formula 1 where U, V and W are hydrogen.

Another aspect of the invention relates to antimycotics which contain compounds of the formula 1 where Z is OR$^{12}$ or SR$^{13}$, and R$^{12}$ and R$^{13}$ have the abovementioned meanings.

Another aspect of the invention relates to antimycotics which contain compounds of the formula 1 where R$^{12}$ and R$^{13}$ are unsubstituted or substituted alkyl, unsubstituted or substituted aryl, or unsubstituted or substituted five- or six-membered hetaryl with 1 to 3 hetero atoms (N, O, S).

Another aspect of the invention relates to antimycotics which contain compounds of the formula 1a

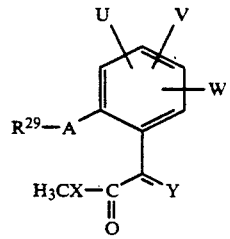

where U, V, W, X and Y have the abovementioned meanings, and —A— is —CR$^{30}$=CR$^{31}$—, —CHR+—CHR$^{31}$—, —O—CHR$^{30}$—, —CHR+—O—, —CHR$^{30}$—S—, —S—CHR$^{30}$—, —O—N=CR$^{30}$— or —CHR$^{30}$—, and where R$^{29}$ is unsubstituted or substituted alkyl, unsubstituted or substituted alkenyl, unsubstituted or substituted aryl, unsubstituted or substituted hetaryl, unsubstituted or substituted aralkyl, unsubstituted or substituted hetarylalkyl, and R$^{30}$ and R$^{31}$ are identical or different and are hydrogen or straight-chain or branched C$_1$-C$_4$-alkyl.

Another aspect of the invention relates to antimycotics which contain compounds of the formula 1a where R$^{29}$—A— is R$^{32}$R$^{33}$C=N—O—CHR$^{31}$— where R$^{31}$ has the abovementioned meanings, and R$^{32}$ and R$^{33}$ are, independently of one another, hydrogen, C$_1$-C$_{12}$-alkyl, C$_1$-C$_4$-haloalkyl, C$_1$-C$_4$-alkoxy-C$_1$-C$_4$-alkyl, C$_1$-C$_{12}$-alkylthio-C$_1$-C$_4$-alkyl, aryl-C$_1$-C$_4$-alkyl, aryloxy-C$_1$-C$_4$-alkyl, arylthio-C$_1$-C$_4$-alkyl, hetaryl-C$_1$-C$_4$-alkyl, C$_2$-C$_{12}$-alkenyl, aryl-C$_2$-C$_4$-alkenyl, hetaryl-C$_2$-C$_4$-alkenyl, C$_2$-C$_{12}$-alkynyl, C$_3$-C$_6$-cycloalkyl, aryl, hetaryl, cyano or one of (a) to (d)

| | |
|---|---|
| COOR$^{34}$ | (a) |
| CONR$^{35}$R$^{36}$ | (b) |
| COR$^{37}$ | (c) |
| CR$^{38}$=NOR$^{39}$ | (d) | or R$^{32}$ and R$^{33}$ form, together with the carbon atom to which they are bonded, a 4- to 7-membered ring which may contain an oxygen or sulfur atom and which may have one or two aromatic rings fused on, e.g. unsubstituted or substituted benzene rings, and $R^{34}$, $R^{35}$, $R^{36}$, $R^{37}$, $R^{38}$ and $R^{39}$ are each hydrogen, $C_1$-$C_4$-alkyl, aryl or hetaryl.

Another aspect of the invention relates to antimycotics which contain compounds of the formula Ia where $R^{29}$ is five- or six-membered aryl which is unsubstituted or substituted one or more times by halogen, $C_1$-$C_{12}$-alkyl, $C_1$-$C_{12}$-haloalkyl, $C_2$-$C_{12}$-alkenyl, $C_2$-$C_{12}$-alkynyl, unsubstituted or substituted aryl, unsubstituted or substituted hetaryl, unsubstituted or substituted aralkyl, $C_1$-$C_{12}$-alkoxy, $C_1$-$C_{12}$-haloalkoxy, $C_2$-$C_{12}$-alkenyloxy, $C_2$-$C_{12}$-alkynyloxy, unsubstituted or substituted aryloxy, formyl, $C_1$-$C_{12}$-acyl, cyano, trifluoromethyl, nitro or —$CR^{34}$=N—$OR^{35}$ and/or may be fused with a benzene ring, or is benzyl or hetaryl, where $R^{34}$ is hydrogen or $C_1$-$C_4$-alkyl and $R^{35}$ is hydrogen, $C_1$-$C_8$-alkyl, $C_2$-$C_8$-alkenyl or $C_2$-$C_8$-alkynyl.

Supplementary reference is made, concerning the preparation of the active substances, to the fact that the compounds where Y has any of the abovementioned meanings can be prepared from the keto esters of the formula 2

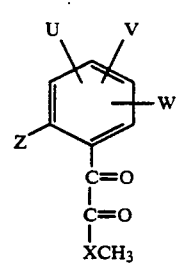

where U, V, W, X and Z have the abovementioned meanings, by known processes.

Furthermore, the preparation of the keto esters 2 is described in the abovementioned publications.

Examples of compounds of the formula I which can be present in the antimycotics according to the invention are listed in Table 1. Other examples are indicated in the European patent applications mentioned.

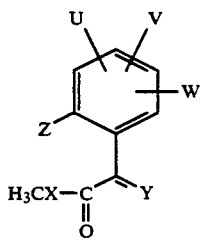

The compounds may occur in isomeric forms in respect of the C=Y double bond. The E isomers are preferred.

TABLE 1

| No. | Z— | U, V, W | =Y | X |
|---|---|---|---|---|
| 1 | 2-methylphenoxymethyl (O—CH₂—) | H, H, H | =CH—OCH₃ (E) | O |
| 2 | 2-methylphenoxymethyl (O—CH₂—) | " | =N—OCH₃ (E) | O |
| 3 | " | " | =CH—CH₃ (E) | O |
| 4 | " | " | =CH—CH₂—CH₃ (E) | O |
| 5 | " | " | =CH—SCH₃ (E) | O |
| 6 | " | " | =N—OCH₃ (E) | NH |
| 7 | 4-(difluoromethoxy)styryl (HF₂C CF₂O—...—CH=CH—) | " | =CH—OCH₃ (E) | O |
| 8 | 2-methylstyryl (—CH=CH—) | " | =N—OCH₃ (E) | O |

TABLE 1-continued

| No. | Z— | U, V, W | =Y | X |
|---|---|---|---|---|
| 9 | 3-methyl-4-(CH₂O-)phenyl with C(=N-OCH₃)-CH₂CH₂CH₃ | " | =N—OCH₃ (E) | O |
| 10 | " | " | =CH—OCH₃ (E) | O |
| 11 | 3-methyl-4-(CH₂O-)phenyl with C(=N-O-allyl)-CH₂CH₂CH₃ | " | =N—OCH₃ (E) | O |
| 12 | " | " | =CH—OCH₃ (E) | O |
| 13 | 2-fluorophenyl-C(cyclopropyl)(C(O)O-CH₂—) | " | =CH—OCH₃ (E) | O |
| 14 | 2,6-difluorophenyl-C(cyclopropyl)(C(O)O-CH₂—) | H, H, H | =CH—OCH₃ (E) | O |
| 15 | " | " | =N—OCH₃ (E) | O |
| 16 | 3-phenylisoxazol-5-yl-CH=CH— | " | =CH—OCH₃ (E) | O |
| 17 | 1-(4-chlorophenyl)pyrazol-4-yl-CH=CH— | " | =CH—OCH₃ (E) | O |
| 18 | 3-bromophenyl-C(=N-O-CH₂—)CH₃ | " | =N—OCH₃ (E) | O |
| 19 | " | " | =CH—OCH₃ (E) | O |
| 20 | 4-methylphenyl-C(=N-O-CH₂—)CH₃ | " | =N—OCH₃ (E) | O |
| 21 | " | " | " | NH |

TABLE 1-continued
| No. | Z— | U, V, W | =Y | X |
|---|---|---|---|---|
| 22 | 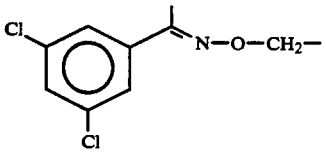 | " | " | O |
| 23 | " | " | " | NH |
| 24 | 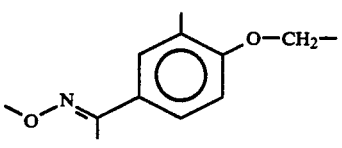 | " | =CH—OCH$_3$ (E) | O |
| 25 | " | " | =CH—CH$_3$ (E) | O |
| 26 | " | " | =CH—CH$_2$—CH$_3$ (E) | O |
| 27 | " | " | =N—OCH$_3$ (E) | O |
| 28 | 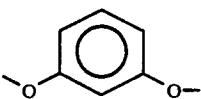 | " | =CH—OCH$_3$ (E) | O |
| 29 | " | " | =N—OCH$_3$ (E) | O |
| 30 | 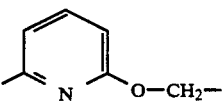 | " | =CH—OCH$_3$ (E) | O |
| 31 | " | " | =N—OCH$_3$ (E) | O |
| 32 | 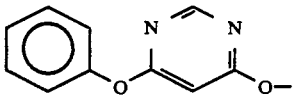 | " | =CH—OCH$_3$ (E) | O |
| 33 | 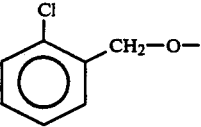 | " | =N—OCH$_3$ (E) | O |
| 34 | 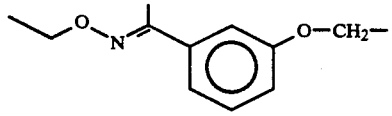 | " | =N—OCH$_3$ (E) | O |
| 35 | 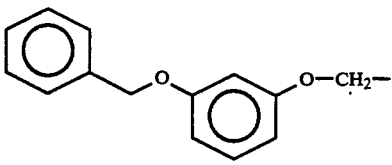 | " | =N—OCH$_3$ (E) | O |
| 36 | 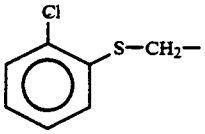 | " | =CH—OCH$_3$ (E) | O |

TABLE 1-continued

| No. | Z— | U, V, W | =Y | X |
|-----|-----|---------|-----|---|
| 37  | (2-cyanophenoxy structure with N=CH-N) | " | =N—OCH$_3$ (E) | O |

Surprisingly, the phenylacetic acid derivatives not only have a very good in vitro antimycotic activity but also a good in vivo activity which can be used therapeutically, especially for dermatophytes, but also for other microorganisms. They also have antibacterial activity. The active substances thus represent a valuable enrichment of pharmacy.

The action on dermatophytes, bacteria and protozoa can be demonstrated by methods as are described, for example, in P. Klein, Bakteriologische Grundlagen der chemotherapeutischen Laboratoriumspraxis, Springer-Verlag, Berlin, 1957. The action on yeasts can be demonstrated in the test on the pseudomycelium or mycelium phase (cf. DE-A 30 20 093).

The minimum inhibitory concentration (MIC) was determined by the agar dilution method of DIN 58 940/ICS.

For this, Petri dishes with a diameter of 9 cm were charged under sterile conditions with 20 ml of freshly prepared Müller-Hinton agar (Merck, Cat. No 5337), which was kept liquid at 50° C., and to which 10% by volume of the particular active substance solution was added. The samples are readily soluble in DMSO. In each case 10.0 mg were dissolved in 10.0 ml of DMSO and further diluted with sterile double-distilled water. The final concentrations after mixing with the test agar are to be found in Table 2. Plates with the highest solvent concentration in each case (control C 1) and with 10% double-distilled water (control C 2) without active substance were used to check growth by comparison.

After solidification and drying (about 1 h at 37° C.) the test plates were inoculated by dotting with 10 μl of the test organism suspensions (inoculum) in each case.

The inocula were prepared in accordance with NCCLS/FDA recommendations. After culturing on solid media and checking purity and identity, some colonies were transferred into sterile Müller-Hinton broth (Merck, Cat. No. 10293) and incubated until turbidity was visible. These cultures were diluted by adding sterile broth until the turbidity corresponded to 0.5 of the McFarland standard (=about 10(8) CFU/ml). A further 1:10 dilution was used as inoculum, and its organism concentration was determined in parallel once again by spiralometer.

The inoculated plates were incubated at 36°±1° C. (bacteria) or 20°±1° C. (fungi) for 24 (bacteria) or 72 (fungi) h and then evaluated.

The complete test was repeated in an independent experiment. The results were reproducible in all cases.

The reported MIC was that concentration of active substance at which no growth was visible on inspection. Minimal, scarcely visible growth or a few small colonies were not counted. On the growth controls without active substance all the test organisms had grown as a spot about 0.5 cm$^2$ in size (precondition for evaluation). The following test organisms were tested as examples (concentration in CFU/ml):

Staphylococcus (S.) aureus ATCC 6538 (1.2×10$^6$)
Pseudomonas (Ps.) aeruginosa ATCC 27853 (1.0×10$^6$)
Escherichia (E.) coli ATCC 8739 (1.4×10$^6$)
Candida (C.) tropicalis DSM 4238 (0.8×10$^6$)
Aspergillus (A.) niger ATCC 16404 (0.9×10$^6$)
Microsporum (M.) canis CBS 38564 (1.0×10$^6$)
Trichophyton (T.) mentagrophytes CBS 26379 (0.9×10$^6$)
T. rubrum DSM 4167 (1.3×10$^6$)
Epidermophyton (E.) floccosum CBS 55384 (1.4×10$^6$)

TABLE 2

Results of the agar dilution tests

Growth of test organisms: +
No growth of test organisms: —
C = controls without active substance MIC in μg/ml

| Test organisms | C 1 | C 2 | Compound of Example No. | | | | | | Example No. | | | | | | | | | |
|---|---|---|---|---|---|---|---|---|---|---|---|---|---|---|---|---|---|---|
| | | | 1 | 2 | 3 | 7 | 8 | 9 | 10 | 11 | 12 | 13 | 14 | 15 | 16 | 17 | 18 | 19 |
| S. aureus | + | + | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 |
| Ps. aeruginosa | + | + | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 |
| E. coli | + | + | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 | >5.0 |
| C. tropicalis | + | + | 0.1 | 0.1 | 0.5 | 0.1 | 0.5 | 0.1 | 0.1 | 0.1 | 0.1 | 0.5 | 0.1 | 0.5 | 0.5 | 0.5 | 0.1 | 0.1 |
| A. niger | + | + | 0.1 | 0.1 | 0.1 | 0.1 | 0.5 | 0.5 | 0.5 | 1.0 | 0.5 | 0.5 | 0.1 | 0.5 | 0.5 | 0.5 | 1.0 | 0.5 |
| M. canis | + | + | 5.0 | 5.0 | 5.0 | 5.0 | 5.0 | 5.0 | 5.0 | 5.0 | 5.0 | 5.0 | 5.0 | >5.0 | 5.0 | 5.0 | 5.0 | 5.0 |
| T. mentagrophytes | + | + | 5.0 | 5.0 | 5.0 | 5.0 | 5.0 | 5.0 | 5.0 | 5.0 | 5.0 | 5.0 | 5.0 | >5.0 | 5.0 | 5.0 | 5.0 | 5.0 |
| T. rubrum | + | + | 5.0 | 5.0 | 5.0 | 5.0 | 5.0 | 5.0 | 5.0 | 5.0 | 5.0 | 5.0 | 5.0 | >5.0 | 5.0 | 5.0 | 5.0 | 5.0 |
| E. floccosum | + | + | 5.0 | 5.0 | 5.0 | 5.0 | 5.0 | 5.0 | 5.0 | 5.0 | 5.0 | 5.0 | 5.0 | >5.0 | 5.0 | 5.0 | 5.0 | 5.0 |

The compounds of the present invention also have good inhibitory effects on the test organisms Exophiola jennselmei.

For example:

| Compound of Example No. | MIC [μg/ml] |
|---|---|
| 1 | 10 |
| 3 | 30 |
| 8 | 10 |
| 10 | 10 |
| 16 | 3 |
| 17 | 3 |
| 19 | 10 |

In the model of guinea pig trichophytosis (Trichophyton mentagrophytes), cf. Heffter-Heubner: Handbuch der exp. Pharmakologie, Vol. XVI/II A, the novel compounds are highly effective on external use without recurrence.

The actions of the test substances on topical use against Exophiola jennselmei as the cause of subcutaneous mycoses and in a model of experimental C. albicans vaginitis were likewise good.

The novel compounds also have oral activity. Good cure rates for infections were obtained after oral administration of low therapeutic doses of the test substances in the model of experimental generalized candidiasis in mice and in the model of experimental vaginitis with Candida albicans in rats.

The compounds are therefore particularly suitable for external as well as oral treatment of fungal infections in humans and animals. Examples of indications for humans and animals are: subcutaneous mycoses and dermatomycoses, especially caused by dermatophytes such as species of the genera Epidermophyton, Microsporum or Trichophyton, yeasts such as species of the genera Candida and molds such as species of the genera Aspergillus, Mucor or Absidia.

The compounds can be used alone or together with other known active substances, especially antibiotics.

The chemotherapeutic agents or formulations are produced with conventional solid, semi-solid or liquid excipients or diluents and the conventional pharmaceutical auxiliaries appropriate for the required mode of administration in a dosage suitable for use in a conventional manner, especially by mixing (cf. H. Sucker et al., Pharmazeutische Technologie, Thieme-Verlag, Stuttgart, 1978).

Examples of suitable dosage forms are uncoated and coated tablets, capsules, pills, aqueous solutions, suspensions and emulsions, sterile injectable solutions, nonaqueous emulsions, suspensions and solutions, ointments, creams, pastes, lotions etc.

The therapeutically active compound is preferably present in pharmaceutical formulations in a concentration of 0.01 to 90% by weight of the complete mixture.

In general, on oral administration both in human and in veterinary medicine, the active substance or substances can be administered in amounts of from about 1.0 to about 50.0, preferably from 2 to 10, mg/kg of body weight per day, preferably in the form of several individual doses to achieve the required results. However, it may be necessary to deviate from the stated dosages, specifically depending on the nature and severity of the disease, the nature of the formulation and of the administration of the drug, and the time or interval over which administration takes place. Thus, in some cases less than the abovementioned amounts of active substances may suffice, whereas in other cases these amounts must be exceeded. Examples of pharmaceutical formulations:

EXAMPLE A

Tablet containing 250 mg of active substance Composition for 1,000 tablets:

| Active substance | 250 g |
|---|---|
| Potato starch | 100 g |
| Lactose | 50 g |
| 4% gelatin solution | 45 g |
| Talc | 10 g |

Production:

The finely powdered active substance, potato starch and lactose are mixed. The mixture is moistened with about 45 g of 4% gelatin solution, granulated and dried. The dried granules are screened, mixed with 10 g of talc and compressed to tablets in a rotary tableting machine. The tablets are packed in tightly closing polypropylene containers.

EXAMPLE B

Cream containing 1% active substance

| Active substance | 1.0 g |
|---|---|
| Glycerol monostearate | 10.0 g |
| Cetyl alcohol | 4.0 g |
| Polyethylene glycol 400 stearate | 10.0 g |
| Polyethylene glycol sorbitan monostearate | 10.0 g |
| Propylene glycol | 6.0 g |
| Methyl p-hydroxybenzoate | 0.2 g |
| Demineralized water | to 100.0 g |

Production:

The very finely powdered active substance is suspended in propylene glycol, and the suspension is stirred into a melt of glycerol monostearate, cetyl alcohol, polyethylene glycol 400 stearate and polyethylene glycol sorbitan monostearate at 65° C. A solution of the methyl p-hydroxybenzoate in water at 70° C. is emulsified in this mixture. After cooling, the cream is homogenized in a colloid mill and packed into tubes.

EXAMPLE C

Dusting powder containing 1% active substance

| Active substance | 1.0 g |
|---|---|
| Zinc oxide | 10.0 g |
| Magnesium oxide | 10.0 g |
| Highly disperse silica | 2.5 g |
| Magnesium stearate | 1.0 g |
| Talc | 75.5 g |

Production:

The active substance is micronized in an air jet mill and mixed homogeneously with the other ingredients. The mixture is passed through a screen (mesh No. 7) and packed in polyethylene containers with perforated cap.

We claim:

1. A process for treating mycoses in humans and nonhuman animals comprising administering a composition comprising an effective amount of an active compound of the formula

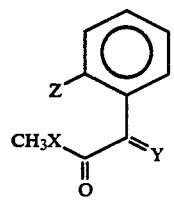

where $=Y$ is $=CH-OCH_3$, $=CH-CH_3$, $=CH-CH_2-CH_3$, $=CH-SCH_3$, or $=N-OCH_3$; X is oxygen, or if Y is =N—OCH₃, also NH; Z is F, Cl, Br, I, nitro, cyano, —OR¹², —SR¹³, —SOR¹⁴, SO₂R¹⁵, —COOR¹⁶, —CONR¹⁷R¹⁸, —COR¹⁹, —CR²⁰=NR²¹, —N=CR²²R²³, —CR²⁴=N—OR²⁵, —CR²⁵R²⁶—O—N=CR²⁷R²⁸, —CR³⁰=CR³¹R²⁹, —CHR³⁰—CHR³¹R²⁹, —O—CHR³⁰R²⁹, —CHR³⁰—OR²⁹, —CHR³⁰—SR²⁹, —S—CHR³⁰R²⁹, —O—N=CR³⁰R²⁹, —CHR³⁰R²⁹; or —R³¹-CH—O—N=CR³³R³²;

R¹² to R²⁹, identical or different, are hydrogen; C₁₋₁₈ alkyl; C₂₋₈ alkenyl; C₂₋₈ alkynyl; a five- or six-membered hetaryl with 1 to 3 atoms selected from the group consisting of N, O and S; a five- or six-membered aryl which can be unsubstituted or substituted 1 or more times with halogen C₁₋₁₂ alkyl, C₁₋₁₂ haloalkyl, C₂₋₁₂ alkenyl, C₂₋₁₂ alkynyl, C₁₋₁₂ alkoxy, C₁₋₁₂ haloalkoxy, C₂₋₁₂ alkenyloxy, C₂₋₁₂ alkynyloxy, formyl, C₁₋₁₂ acyl, cyano, trifluoromethyl, nitro or —CR⁴⁰=N—OR⁴¹ where R⁴⁰ is H or C₁₋₄ alkyl and R⁴¹ is H, C₁₋₈ alkyl, C₂₋₈ alkenyl, or C₂₋₈ alkynyl;

R³⁰ and R³¹, identical or different, are H or a straight chain or branched C₁₋₄ alkyl;

R³² and R³³, the same or different, are H, C₁₋₁₂ alkyl, C₁₋₄ haloalkyl, C₁₋₄ alkoxy-C₁₋₄ alkyl, C₁₋₄ haloalkyl, C₁₋₄ alkoxy-C₁₋₄-alkyl, aryloxy-C₁₋₄ alkyl, arylthio C₁₋₄ alkenyl, hetaryl-C₂₋₄ alkenyl, C₂₋₁₂-alkynyl, C₃₋₆-cycloalkyl, aryl, hetaryl, cyano, —COOR³⁴, —CONR³⁵R³⁶, —COR³⁷, —CR³⁸—NOR³⁹ or R³² and R³³ form, together with the carbon atom to which they are bonded, a 4- or 7-membered ring which can contain an oxygen or sulfur atom;

R³⁴ to R³⁹ are H, C₁₋₄ alkyl, aryl or hetaryl;

wherein said aryl is a five- or six-membered ring which is unsubstituted or substituted 1 or more times with halogen, C₁₋₁₂ alkyl, C₁₋₁₂ haloalkyl, C₂₋₁₂ alkenyl, C₂₋₁₂ alkynyl, C₁₋₁₂ alkoxy, C₁₋₁₂ haloalkoxy, C₂₋₁₂ alkenyloxy, C₂₋₁₂ alkynyloxy, formyl, C₁₋₁₂ acyl, cyano, trifluoromethyl, nitro or —CR⁴⁰=N—OR⁴¹ where R⁴⁰ is H or C₁₋₄ alkyl and R⁴¹ is H, C₁₋₈ alkyl C₂₋₈ alkenyl or C₂₋₈ alkynyl; and said hetaryl is a five- or six-membered ring with 1 to 3 atoms selected from the group consisting of N, O and S.

2. The process according to claim 1, wherein said composition further comprises a solid, semi-solid or liquid excipient or diluent.

3. The process according to claim 1, wherein said active compound is administered in an amount of from about 1.0 to about 50.0 mg/kg of body weight per day.

4. The process according to claim 1, wherein 0.01 to 90% by weight, based on the total weight of the composition, of said active compound is present in said composition.

5. A process for treating mycoses in humans and nonhuman animals comprising administering a composition comprising an effective amount of an active compound of the formula

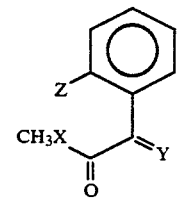

where
=Y is =CH—OCH₃, =CH—CH₃, =CH—CH₂—CH₃, =CH—SCH₃, or =N—OCH₃;
X is oxygen, or if Y is =N—OCH₃, also NH:
Z is

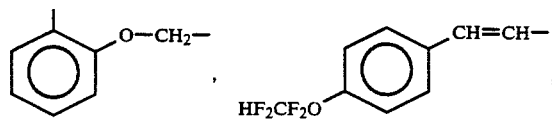

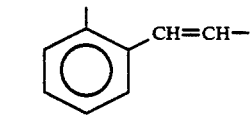

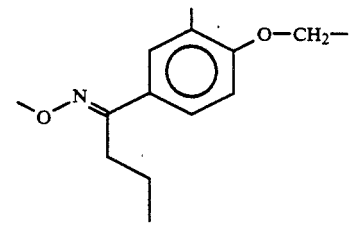

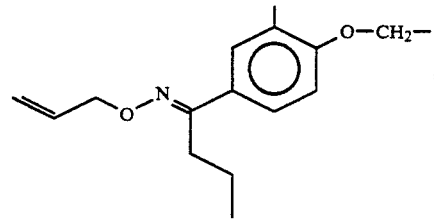

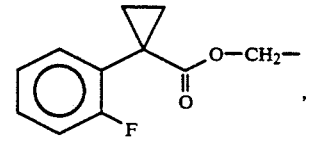

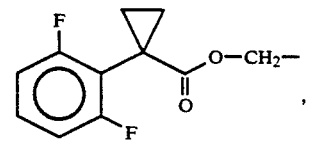

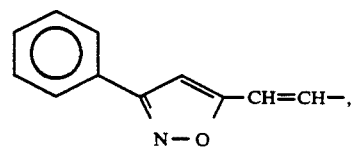

-continued
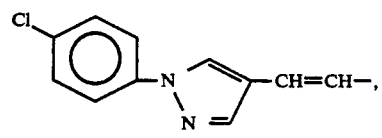
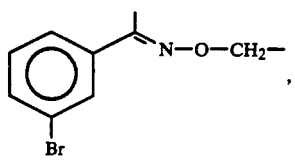
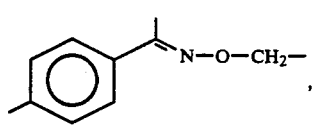
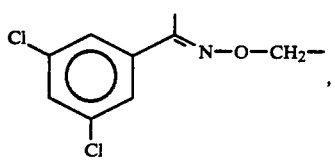
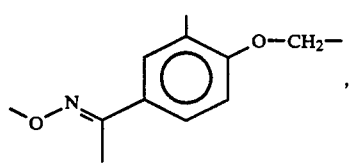
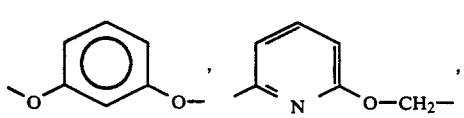
-continued
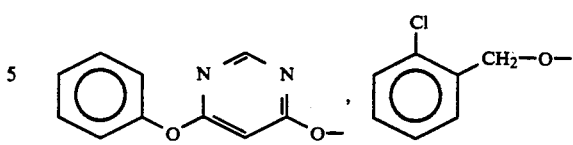
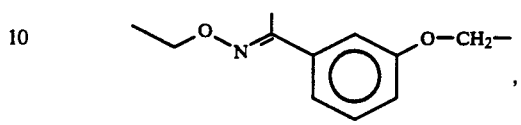
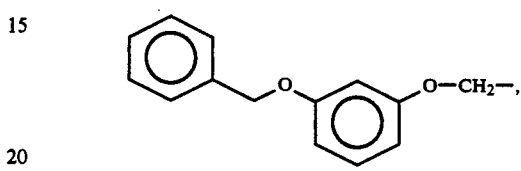
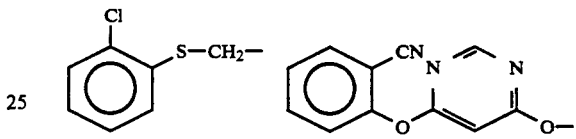
6. The process according to claim 5, wherein Z is
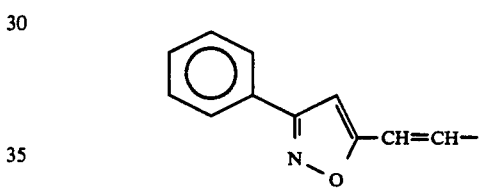
Y is $=CH-OCH_3$, and
X is O.
* * * * *